United States Patent [19]

Bird

[11] Patent Number: 4,742,823

[45] Date of Patent: May 10, 1988

[54] LIQUID INJECTOR FOR WETTING MECHANICALLY DELIVERED INTRAPULMONARY GASSES

[76] Inventor: Forrest M. Bird, P.O. Box 817, Sandpoint, Id. 83864

[21] Appl. No.: 901,890

[22] Filed: Aug. 29, 1986

[51] Int. Cl.⁴ .................................. A61M 15/00
[52] U.S. Cl. ......................... 128/203.12; 128/203.25
[58] Field of Search ............... 128/200.14, 200.18, 128/200.19, 200.21, 203.25, 204.25, 200.11, 204.14; 239/366; 261/78 A, DIG. 65, 67

[56] References Cited

U.S. PATENT DOCUMENTS

| | | | |
|---|---|---|---|
| 2,206,688 | 7/1940 | Bloomheart | 128/203.25 |
| 2,835,267 | 5/1958 | Andresen et al. | 239/366 |
| 2,887,181 | 5/1959 | Dillon | 239/366 |
| 2,899,018 | 8/1959 | Booth | 239/366 |
| 4,101,611 | 7/1978 | Williams | 261/78 A |
| 4,508,117 | 4/1985 | Rodari | 128/204.25 |
| 4,589,409 | 5/1986 | Chatburn et al. | 128/204.25 |

FOREIGN PATENT DOCUMENTS 1367140  6/1984  France ................. 239/366

Primary Examiner—Edward M. Coven
Assistant Examiner—J. P. Lacyk
Attorney, Agent, or Firm—Flehr, Hohbach, Test, Albritton & Herbert

[57] ABSTRACT

Liquid injector for wetting mechanically delivered intrapulmonary gases having a reservoir adapted to contain a quantity of liquid. A tube extends downwardly into the reservoir to a level below the level of the liquid in the reservoir. A one-way check valve controls the flow of liquid from the tube. Tubing including an additional one-way check valve is provided for delivering gas under pressure to the reservoir above the liquid in the reservoir to apply pressure to the liquid in the reservoir to force the liquid up through the tube. An orifice is provided which is in communication with the first named one-way check valve means. A body is provided forming a chamber surrounding the orifice. A valve is provided for adjusting the flow of liquid from the orifice. Gas under pressure is supplied to the chamber to cause the gas to come in contact with the liquid passing through the orifice means. Gas is withdrawn from the chamber after liquid has been introduced into the gas.

19 Claims, 2 Drawing Sheets

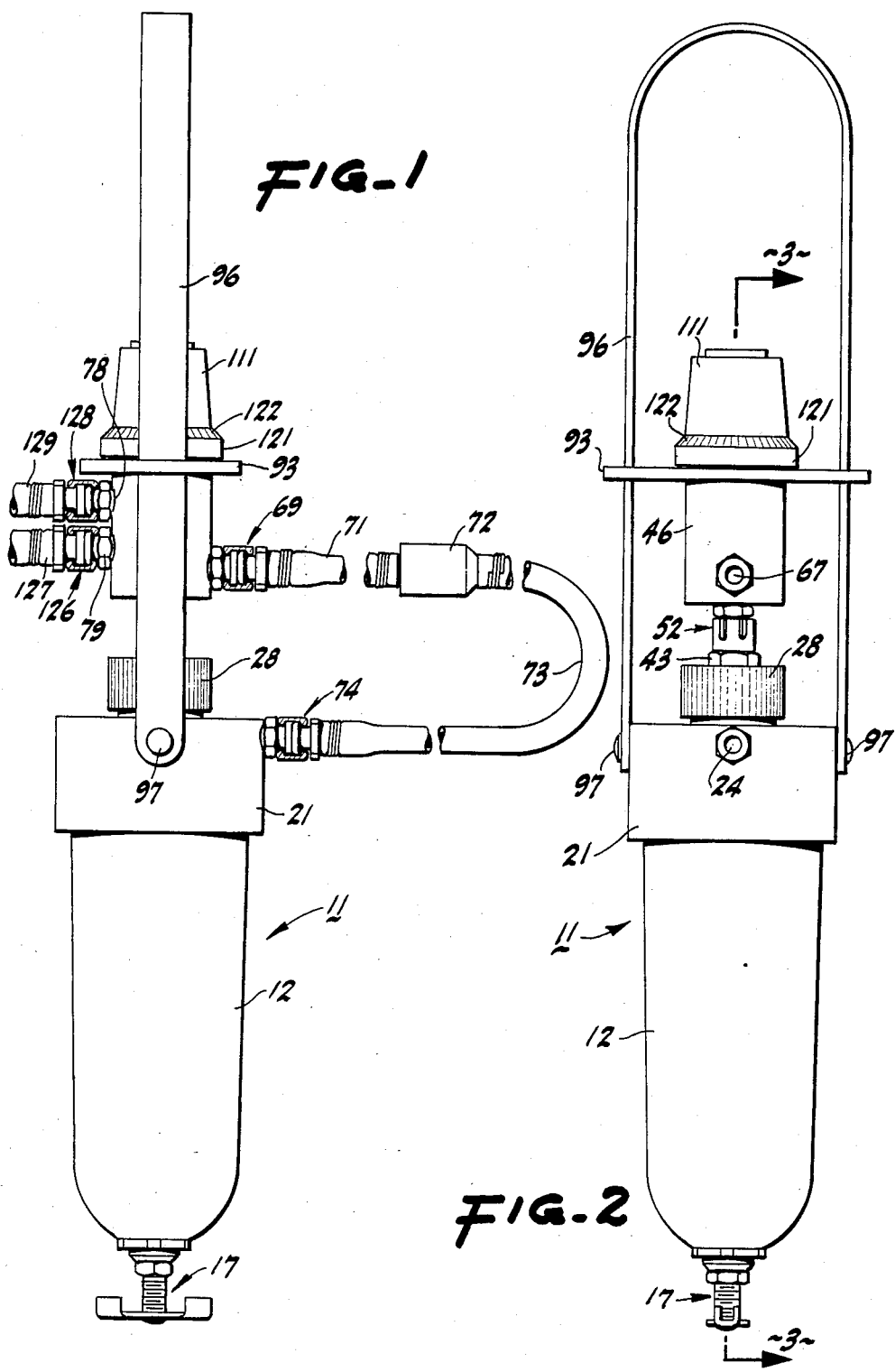

LIQUID INJECTOR FOR WETTING MECHANICALLY DELIVERED INTRAPULMONARY GASSES

This invention relates to a liquid injector for wetting mechanically delivered intrapulmonary gasses and, more particularly to an injector for wetting pulses mechanically delivered intrapulmonary gasses.

Heretofore nebulizers have been provided such as those disclosed in U.S. Pat. No. 3,353,536 which have been utilized for the humidification or nebulization of gasses supplied to the pulmonary structures of patients with mechanical flow generation by diffusive and/or convective type ventilation. With the advent of devices such as those disclosed in U.S. Pat. No. 4,592,349 in which there is a jet type of delivery of gasses to the proximal airway of the patient, it has been found that it is difficult to deliver adequate moisture to sufficiently humidify the gasses so that the patient is not dehydrated. Other types of devices for delivering gases to patients such as wick type devices, as disclosed in co-pending application Ser. No. 866,791, filed May 23, 1986, it is not feasible to deliver sufficient water to the wicks to provide adequate humidification in a number of applications. Additional problems are encountered in ventilators and respirators of the type in which it is necessary to deliver gases to operate humifidiers or nebulizers in certain situations as, for example, where it is necessary to transport patients from a site of trauma to an institution where the source of respiratory gases during transport may be limited. Therefore a different approach is required to deliver the desired humidification to the gases being supplied to the patient. There is therefore a need for a new and improved device for wetting mechanically delivered intrapulmonary gasses to patients.

In general, it is an object of the present invention to provide a liquid injector for wetting mechanically delivered intrapulmonary gasses which greatly reduces the amount of gases required for operation of the same.

Another object of the invention is to provide an injector of the above character which makes it possible to deliver water into high pressure airstreams.

Another object of the invention is to provide an injector of the above character in which the water can be introduced directly through the jets of gases.

Another object of the invention is to provide an injector of the above character in which water particles are injected directly into the jet orifice when very low intrapulmonary compliance exists requiring high peak delivery pressures.

Another object of the invention is to provide an injector of the above character in which predetermined amounts of water can be injected through the jets of gasses.

Another object of the invention is to provide an injector of the above character which can be economically manufactured.

Additional objects and features of the invention will appear from the following description in which the preferred embodiments are set forth in detail in conjunction with the accompanying drawings.

FIG. 1 is a side elevational view of a liquid injector for mechanically delivered intrapulmonary gasses incorporating the present invention.

FIG. 2 is a front elevational view of a liquid injector shown in FIG. 1.

Figure 3:
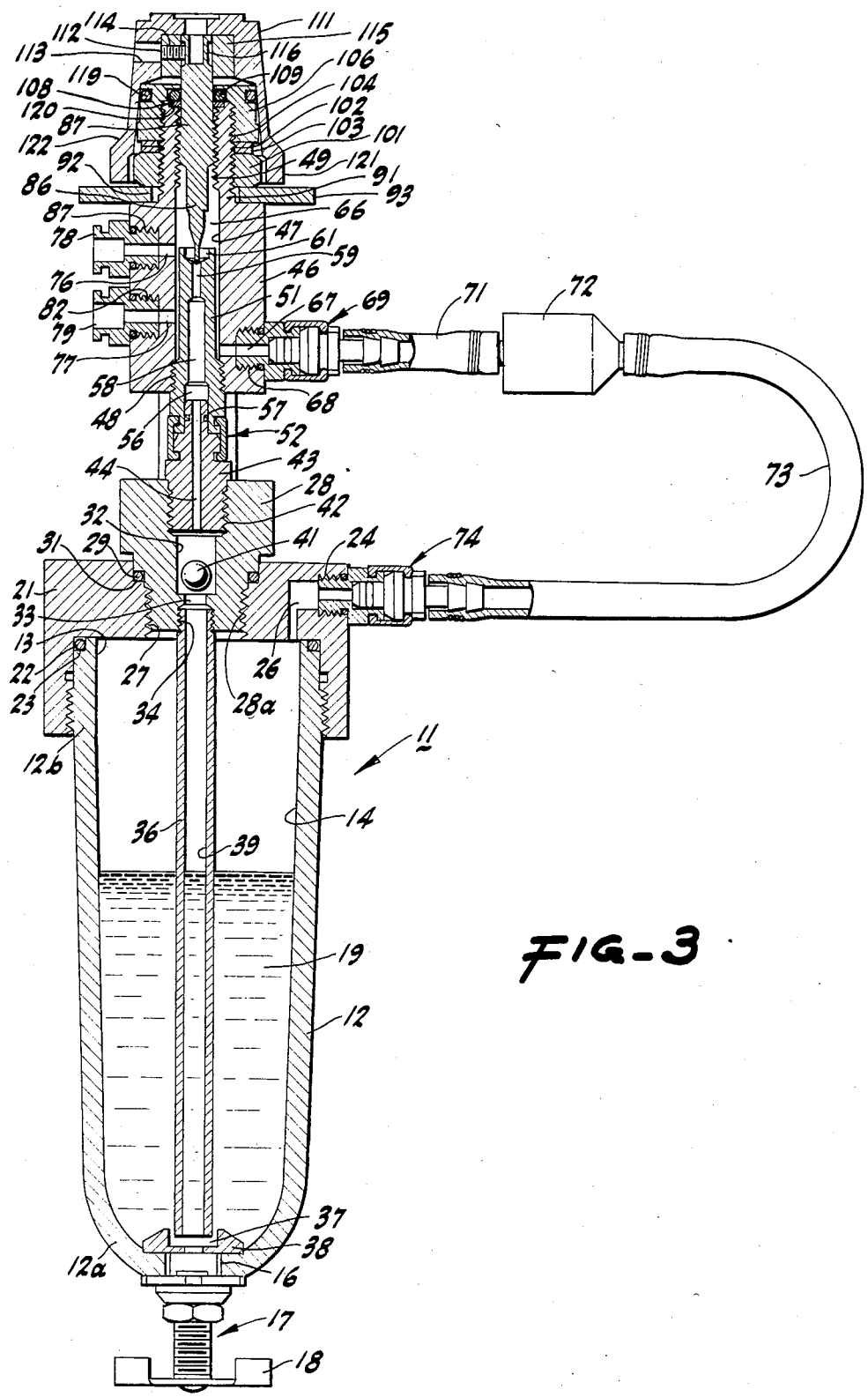
FIG. 3 is a cross sectional view taken along the line 3—3 of FIG. 2.

In general, the liquid injector for wetting mechanically delivered intrapulmonary gasses is comprised of a reservoir adapted to contain a quantity of liquid having a tube extending downwardly into the reservoir to a level below the level of the liquid in the reservoir. A one-way check valve is provided for controlling the flow of liquid from the tube. Tubing including a one-way check valve is provided for delivering gas under pressure to the reservoir above the liquid in the reservoir to apply pressure to the liquid in the reservoir to force the liquid up through the tube. Orifice means is provided which is in communication with the one-way check valve means. Means is provided for forming a chamber surrounding the orifice means.

Valve means is provided for adjusting the flow of liquid from the orifice means. Means is provided for supplying gas under pressure to the chamber to cause the gas to come in contact with the liquid passing through the orifice means. Means is provided for withdrawing gas from the chamber after liquid has been introduced into the gas.

More in particular as shown in the drawings, the liquid injector 11 for wetting mechanically delivered intrapulmonary gases consists of a reservoir or bowl 12. The reservoir 12 is generally cylindrical and is circular in cross section. It is provided with a lower cup-shaped portion 12a and an open top portion 12b which is provided with an opening 13 which opens into a chamber 14. The reservoir or bowl 12 can be formed of a suitable material such as a transparent plastic. It is provided with a hole 16 extending through the cup-shaped portion 12a which has a conventional drain assembly 17 mounted therein and which is provided with a wing nut or screw 18 which can be rotated to move the drain assembly 17 between open and closed positions so that a liquid 19 such as water within the bowl 12 can be drained therefrom.

A reservoir manifold cap 21 is threadedly mounted on the upper extremity of the reservoir or bowl 12 so that it can be readily removed therefrom to permit filling of the bowl 12 through the opening 13 with a liquid 19. If additional reservoir capacity is desired this can be readily accomplished by installing an auxillary reservoir in series with the main reservoir 12.

An O-ring 22 is mounted in a recess 23 provided on the upper extremity of the bowl 12 and serves to form a liquid-tight seal between the cap 21 and the bowl 12. The cap 21 can be formed of a suitable material such as plastic. The cap 21 is provided with a threaded port 24 that opens into a passage 26 which opens into the interior of the bowl 12. As hereinafter described, the port 24 serves as a reservoir charging port. The cap 21 is also provided with a centrally disposed threaded bore 27 which receives the capillary cap 28 formed of a suitable material such as plastic which is provided with a threaded portion 28a that is threaded into the threaded bore 27. The cap 28 can be knurled as shown. An O-ring 29 seated in an annular recess 31 provided in the cap 21 serves to establish a liquid-tight seal between the capillary cap 28 and the reservoir manifold cap 21. The cap 28 is provided with a centrally disposed bore 32 which opens into a passage 33. The passage 33 opens into a threaded bore 34 which has downwardly extending capillary tube 36 threadedly mounted therein. The capillary tube 36 extends downwardly into the bottom extremity of the chamber 14 formed within the bowl.

The lower extremity of the tube 36 is loosely seated within a cylindrical recess 37 provided in the fitting 38 forming a part of the drain assembly 17. The capillary tube 36 is provided with a passage 39 which opens into the recess 37 and into the passage 33.

A ball check 41 is provided in the bore 32 and serves as an anti-back flow and surge protection device. The bore 32 opens into a threaded bore 42. A fitting 43 is threadedly mounted in the threaded bore 42 and has a flow passage 44 extending therethrough.

A cylindrical body 46 formed of a suitable material such as transparent plastic is provided as a part of the liquid injector. The body 46 is provided with a chamber or bore 47 which extends axially thereof and opens into a threaded bore 48 at one end and a threaded bore 49 at the other end. A post 51 is threaded into the threaded bore 48 and extends upwardly into the bore chamber 47. A quick disconnect assembly 52 of the type described in co-pending application Ser. No. 671,491, filed Nov. 14, 1984, is utilized for connecting the lower extremity of the post 51 to the fitting 43. The post 51 is provided with a bore 56 which receives the fitting 43. An O-ring 57 is provided on the fitting 43 to provide a liquid-tight seal between the fitting 43 and the post 51. The bore 56 provided on the post 51 opens into a smaller bore 58 extending axially of the post 51 and is in communication with a still smaller bore 59 axially aligned with the bore 58 and which opens through an orificial well 61 that opens into the interior of the bore or chamber 47. The bore or chamber 47 at this portion of the same forms a aerosol mixing chamber as hereinafter described.

The post 51 is sized in such a manner so that there is an annular space 66 provided between the post and the bore 47. This annular space 66 is in communication with a flow passage 67 extending radially of the body 46. The passage 67 opens into a threaded bore 68 which has a quick disconnect fitting 69 of the type hereinbefore described threadedly mounted therein. A tube 71 is connected to the fitting 69 and is connected to a directional check valve assembly 72 of a type which permits gas flow in a direction from the passage 67. The check valve 72 is connected by tubing 73 to a quick disconnect fitting 74 threaded into the bore 24 of the cap 21.

Additional flow passages 76 and 77 are provided in the body 46 extending radially of the body and are in communication with the space 66 and the bore 47. Fittings 78 and 79 are provided in threaded bores 81 and 82 in communication with the passages 76 and 77. The fitting 78 serves as a downdraft inlet service socket and fitting 79 serves as the updraft inlet service socket. Therefore, respiratory gases can flow downward through inlet fitting 78 and outflow through fitting 79 for a downdraft configuration or conversely, respiratory gases can flow into fitting 79 upward with outflow through fitting 78 for an updraft configuration. A stepped liquid metering valve member 86 is provided which has an integral stem 87 threaded into the threaded bore 49 of the body 46.

The body 46 is provided with a cylindrical boss 91 which extends through a hole 92 provided in an index panel 93. The index panel 93 is provided with a pair of lots in opposite ends of the same which receive opposite sides of a U-shaped bail or handle 96. The lower extremities of the bail or handle 96 are pivotally secured to the upper extremity of the cap 21 by suitable means such as screws 97 threaded into the cap 21.

The bail or handle 96 makes it possible to hang the liquid injector from a convenient IV stand. It should be appreciated that if desired, the reservoir 12 and the body assembly 46 can be separated from each other and interconnected by appropriate tubing. The handle or bail 96 provides a guide for the index panel 93. In addition to serving as an index panel, it serves as a stabilizer bar to maintain the vertical alignment of the components of the liquid injector as well as to provide an additional support for the body 46.

A nut 101 is threaded onto the body 46. A pair of cam stop rings 102 and 103 are mounted on the boss 91 and overlie the nut 101. A retention cap 106 is also threadedly mounted on the threaded portion 104 and retains the rings 102 and 103 on the boss 91.

The threads provided in the threaded bore 49 and on the stem 87 are very fine threads as, for example, as many as 80 threads per inch to provide for a very fine adjustment of the stepped liquid metering valve 86. A small washer 108 formed of a suitable material such as plastic is disposed on the stem 87 immediately above the threaded portion and is overlaid by an O-ring 109 of a suitable material such as rubber.

The retention cap 106 is mounted in a metering knob 111 in a suitable manner such as by friction fit. The retention cap 106 can be formed of a suitable metal such as brass and the metering knob 111 can be formed of a suitable material such as plastic. The metering knob 111 with the retention cap 106 is rotatably retained on the upper extremity of the stem 87 by set screws 112. The set screws 112 are inserted through openings 113 provided in the knob 111 and threaded into threaded bores 114 provided in a knob insert 115. The set screws 112 seat in an annular recess 116 provided on the upper extremity of the stem 87. Another O-ring 119 is carried by the upper extremity of the retention cap 106 and is adapted to engage the inner wall of the control knob 111 to provide a friction seal between the retention cap 106 and the metering knob 111.

The metering knob 111 is provided with a flange 121 extending radially outwardly therefrom and is provided with a tapered surface 122 which can bear suitable indicia, as for example, the numerals 1 to 12 equally spaced circumferentially on the surface 22. A fitting 126 is mounted on the fitting 79 and is connected to a flexible tip 127 which is adapted to be connected to the device for ventilating a patient. Similarly, a fitting 128 is mounted on the fitting 78 and is connected to tubing 129 which is also connected to the apparatus with which the device is to be utilized.

Operation and use of the liquid injector for wetting mechanically delivered intrapulmonary gases as, for example, pulsed intrapulmonary gases such as that supplied by apparatus of the type described in copending. U.S. application Ser. No. 671,491, filed Nov. 14, 1984, may now be briefly described as follows. The liner tube which is normally utilized for supplying gas to the combination venturi and exhalation valve assembly described in said co-pending U.S. application Ser. No. 671,491, filed Nov. 14, 1984 is connected. This tube, identified as tube 127, is connected to the port or fitting 79 which delivers gas through the passage 77 into the annular space 66 of the stand pipe formed by the post 51 in the chamber 47. The gas, as it enters the space 66, impinges upon the stand pipe formed by the post 51 and flows upwardly around the stand pipe across the top of the orificial well 61.

At the same time that this is occurring, gas from the annular space 66 is also delivered through the flow passage 67 and through the fitting 69 and through the one-way check valve 72 through the tubing 73 into the fitting 74 and into the passage 26 to supply pulses of gas under pressure on top of the liquid 19 within the chamber 14 of the reservoir or bowl 12 to pressurize the top of the liquid 19 in the reservoir. This pressure on the liquid 19 forces the liquid 19 up through the passage 39 in the capillary tube 36 up and into the bore 32 past the ball check 41. The ball check 41 serves to let fluid out of the reservoir but prevents pressure from being applied in an opposite direction to the reservoir 12.

A very few pulses of gas delivered in the chamber 14 will cause the space above the liquid 19 in the bowl or reservoir 12 to be pressurized so that thereafter with each pulse of gas supplied there will be additional liquid supplied through the capillary tube 36 upwardly through the bore 56 and thence into the orifice 61 which is of relatively small diameter as, for example, 0.008 inch where it is delivered into the orificial well 61. The position of the fine stepped metering valve 86 with respect to the orifice 59 determines the size of the orifice and the quantity of liquid which will flow through the orifice.

It should be appreciated that when the gas in the chamber formed by the bore 47 is at the same pressure as the gas in the chamber 14 above the liquid 19, no liquid will flow upwardly into the well 61. Thus during the inspiratory or delivery phase of the ventilator or respirator, no flow of liquid into the well 61 will occur. However, during an expiratory phase, the gas pressure in the chamber 47 will be reduced and liquid will flow up into the well 61 to at least partially fill up the well. As soon as the expiratory phase has been completed and the inspiratory phase occurs, the pressure in the chamber formed by the bore 47 is again increased. However, the liquid in the well 61 cannot go back into the reservoir 12 because of the ball check 41 that prevents such flow. Thus the liquid in the reservoir 61 is trapped and it is this liquid which is vaporized during the inspiratory phase and is delivered through the fitting 78 into the tubing 129 which is connected into the jet of the combination venturi and exhalation valve assembly.

Thus it can be seen that the well 61 is filled during the expiratory phase and that the liquid in the well 61 is taken up or vaporized during the inspiratory phase. The amount of liquid which is introduced into the well during the expiratory phase is controlled by the adjustment of the stepped liquid metering valve 86 which can be adjusted by the rotation of the knob 111.

The liquid injector is constructed in such a manner so that there is a substantially constant pressurization of the chamber 14 above the liquid 19. Thus it can be seen that a measured or metered amount of liquid can be introduced during each inspiratory phase.

When gas is delivered to the bottom side port 79 and gas is taken out of the top side port 78, this can be described as updraft carburation. Conversely, when gas is introduced through the upper side port 78 and taken out of the lower side port 79 this can be described as downdraft carburation. In downdraft carburetion, when the gas is delivered through the side port 78, the gas is blown across the top of the orifice well 61 to fracture the liquid therein and to cause it to swirl downwardly around the stand pipe provided by the post 51 before it exits through the side port 79. In this way, the liquid is thoroughly intermixed with the gas by the time it leaves the side port 79.

Once the liquid reservoir 12 has been charged with several pulses of inspiratory gases, the displacement volume of the charging gas will be equal to the amount of liquid delivered into the respiratory pulse gases and can range from 10 to 100 cc per hour. The tube 36 which reaches into the lower extremities of the reservoir 12 with the liquid in the chamber 12 under pressure delivers liquid into the ball checked plenum formed by the bore 32. The liquid after passing through the ball checked plenum still under pressure enters the metering valve orifice provided by the bore 59. This orifice is surrounded by the orificial well 61. The well as hereinbefore described is provided in the upper extremity of the post 51 which rises through a cylindrical bore 47 to provide a mixing chamber which is circular in cross section and in which a substantial annular space 66 is provided between the post 51 and the bore 47. The height of the post 51 in the bore 47 is sufficient so as to permit the three ports 69, 78 and 79 to be provided at three levels in the annular space 66. The bore 47 also is of a sufficient size so that a relatively large mixing chamber is provided above the orificial well.

The stepped liquid metering valve 86 has a lengthy step down in diameter from the threaded portion of the stem 87 to the tip. The major reduction in stem diameter therefore does not substantially reduce the storage capacity of the orificial well 61. The step down in the valve 86 also increases the size of the mixing chamber above the well and makes it possible to obtain a clear view of the mixing functions taking place within the chamber through the transparent body 46. The metering of the liquid for aerosolization or mixing is facilitated by the use of a small variable orifice provided by the bore 59 of the metering valve 86 which in cooperation with each other provides a small variable orifice of considerable length which provides a precisely variable viscous flow resistance. The extremely fine threads provided on the metering valve stem 87 provide a very gradual transitional movement of the metering valve 86 during rotation of the knob 111. The knob 111 is rotatably stopped within a certain range as, for example, 340 degrees by the internally adjustable cammed stops provided by the cam stop rings 102 and 103 that are utilized to limit rotation to prevent damaging the delicate stainless steel metering valve tip which might be occasioned by hard rotational shut off forces. In addition, the adjustable cam stops prevent excessive liquid delivery into the orificial well 61.

Gas pulses are delivered during the inspiratory phase of the respirator to either of the side ports 78 and 79 which causes gas to be delivered through the side delivery port 69 through the sleeved one-way check valve 72 to the charging port 74 to pressurize the liquid in the reservoir 12. After a few pulses, the liquid in the reservoir 12 is pressurized to the peak pulse delivery pressure. If any liquid has overflowed from the orificial well 61, the liquid will flow down around the post 51 and can be redelivered to the reservoir 12 through the one-way check valve 72 through the charging port 74.

Assuming that the gas pulses are delivered to the lower side port 79, the gas pulses will swirl upwardly around the post 51 and around the shrouded orificial well 61 to cause liquid overflowing from the well to be dispatched in droplets moving upwardly within the mixing chamber provided above the well by the bore 47. In addition, the up flow of gas pulses around the stepped down metering valve 86 above the well creates liquid up flow from the orificial well toward the top of the mixing chamber. Alternatively, if gas pulses are delivered into the top side port 78, a downdraft is created. Gas pulses inflowing at a high velocity pass across the top of the orificial well 61 and serve to convert the liquid in the well to particles and to cause the gases containing liquid particles to swirl downwardly in the annular space 66 to cause a thorough intermixing of the same after which the gas passes out through the lower side port 79. As the pulses pass across the top of the orificial well 61, a venturi-like effect is created which creates an additional pressure drop across the liquid metering orifice formed by the bore 59 to induce adequate liquid refilling of the well from the tube 36.

The turbulence which occurs within the mixing chamber above the post 51 is adequate to cause the liquid to be broken up into small particles and to be thoroughly mixed with the air. Additional intermixing of the liquid particles and the air occurs in the tubing connected to the side port utilized for the exit.

As pulsed respiratory gasses are delivered to either the socket 78 and 79, the gas pressure in the chamber above the metering orifice provided is periodicially decreased in phase with the expiratory and inspiratory phases of the respirator or ventilator supplying gases to the side port 78 or 79. As each pressure decrease occurs, additional liquid will be delivered to the orificial well 61 because of the pressurized liquid within the reservoir 12. As hereinbefore explained back flow of liquid within the tube 36 is prevented by the ball check valve 41.

In the event that the body 46 is separated from the capillary cap 28 through the quick disconnect assembly 52, the ball check valve 41 will move upwardly to occlude the flow passage 44 to prevent pressurized liquid from escaping from the reservoir 12.

It should be appreciated that the volume of the mixing chamber provided above the orificial well 61 should be as small as possible to avoid stroke volume absorption during sub-tidal intrapulmonary delivery of gasses by a respirator. A large mixing chamber would dampen the percussive flow velocity and break down the clinical efficacy by reducing intrapulmonary mechanical mixing. Therefore it is important that there be an in-line liquid injection into the mainstream of pulsed intrapulmonary gas flow supplied to the patient.

The injector delivers or injects periodically a pulse of water in each inspiratory phase to ensure that the inspiratory gases are wetted sufficiently. This prevents dehydration of the lung in the event the patient is being supplied with dry respiratory gasses as, for example, dry oxygen. The device of the present invention is effective in delivering water against high pressure, as for example, as high as 25 psi. For example, this makes it possible to deliver water into gas that is being supplied to the venturi of the jet for the combination venturi and exhalation valve assembly disclosed in U.S. Pat. No. 4,592,349. Also it should be appreciated that the present device can be utilized for injecting water in high pressure systems of types other than that disclosed in U.S. Pat. No. 4,592,349 such as needles, trocars, catheters, etc. Although the present invention has been described principally for the purpose of injecting water into high pressure gas streams, it should be appreciated that other types of liquid such as liquid medication can be introduced in this manner if desired.

What is claimed is:

1. In a liquid injector for wetting mechanically delivered intrapulmonary gases to the airway of a patient, a reservoir adapted to contain a quantity of liquid, a tube extending downwardly into the reservoir to a level below the level of the liquid in the reservoir, one-way ball check valve means controlling the flow of liquid from the reservoir and through the tube, means forming an orifice in communication with the one-way ball check valve means, means forming a chamber surrounding the orifice and overlying the orifice, an orifice well disposed in the chamber encircling the orifice serving to collect liquid as liquid passes through the orifice, valve means extending downwardly into the orifice for adjusting the flow of liquid from the orifice, means for supplying gas under pressure to the chamber to cause the gas to come in contact with the liquid passing through the orifice in a region above the liquid , means in communication with the chamber including one-way check valve means for delivering gas under pressure to the reservoir above the liquid in the reservoir to apply pressure to the liquid in the reservoir to force the liquid up through the tube and through the orifice into the orifice well, and means adapted to be coupled to the airway of the patient for withdrawing gas from the chamber after liquid has been introduced into the gas to supply wetted gases to the airway of the patient.

2. A liquid injector as in claim 1 wherein said means forming an orifice comprises a post extending upwardly into the chamber, wherein a hole extends through the post to form the orifice, wherein the orificial well is provided in the upper extremity of the post, wherein an annular space is formed surrounding the post and wherein said means for supplying gas under pressure and said means for withdrawing gas includes first and second spaced apart ports in communication with the annular space.

3. A liquid injector as in claim 2 wherein said means for delivering gas under pressure to the reservoir includes an outlet port in communication with the annular space.

4. In a liquid injector for wetting mechanically delivered intrapulmonary gases to the airway of a patient, a reservoir adapted to contain a quantity of liquid and having an open top , a reservoir cap removably mounted on said reservoir, means carried by the reservoir cap forming a plenum, check valve means disposed in the plenum, a tube connected to the means forming a plenum and in communication with the plenum and extending downwardly into the lower extremity of the reservoir, said check valve means serving to prevent back flow of liquid from the plenum into the tube, a body providing a mixing chamber, a post extending upwardly into the mixing chamber, a hole extending through the post and providing an orifice in communication with the mixing chamber and in communication with the plenum, inlet and outlet ports carried by the body in communication with the mixing chamber, an additional port carried by the body in communication with the mixing chamber, means connecting the additional port in the body to the interior of the reservoir whereby when gasses are supplied to the inlet port, gas is supplied to the mixing chamber and to the additional port and to the reservoir so that gas impinges on the liquid passing from the orifice in a region above the orifice and adjustable valve means extending downwardly into the orifice for controlling the rate of flow of liquid from the orifice.

5. A liquid injector as in claim 4 wherein said means connecting the additional port to the reservoir includes one-way valve means.

6. A liquid injector as in claim 4 wherein said post is provided with an orificial well in the upper extremity thereof which encircles the orifice and collects liquid flowing from the orifice.

7. A liquid injector as in claim 6 wherein the post and the body provides an annular space surrounding the post and wherein the inlet and outlet ports carried by the body are in communication with the annular space.

8. A liquid injector as in claim 6 wherein said adjustable valve means includes threaded valve stem and means for biasing the valve stem so that a pressure is applied to the valve stem in a direction parallel to the axis of rotation of the valve stem to minimize backlash.

9. In a liquid injector for wetting mechanically delivered intrapulmonary gases, a reservoir adapted to contain a quantity of liquid and having an open top, a reservoir cap removably mounted on said reservoir, means carried by the reservoir cap forming a plenum, check valve means disposed in the plenum, a tube connected to the means forming a plenum and in communication with the plenum and extending downwardly into the lower extremity of the reservoir, means forming an orifice in communication with the mixing chamber and in communication with the plenum, inlet and outlet ports carried by the body in communication with the mixing chamber, an additional port carried by the body in communication with the mixing chamber, means connecting the additional port in the body to the interior of the reservoir whereby when gasses are supplied to the inlet port, gas is supplied to the mixing chamber and to the additional port and to the reservoir, means for controlling the rate of flow of liquid from the orifice, a U-shaped handle secured to said reservoir cap and a member slidably mounted on said U-shaped handle and engaging said body to support said body.

10. A liquid injector as in claim 9 together with quick disconnect means connecting said body to said reservoir cap.

11. A liquid injector as in claim 9 together with a control knob mounted on said adjustable valve means and overlying said slidable member.

12. In a method for delivering a liquid for wetting mechanically delivered intrapulmonary gases to the airway of a patient from a reservoir containing the liquid and by the use of a mixing chamber having an orifice therein, supplying gas under pressure through the reservoir to pressurize the liquid in the reservoir, delivering pressurized liquid from the reservoir to the orifice into the mixing chamber, supplying gas in pulses under pressure to the mixing chamber to cause the gas to come in contact with the liquid passing from the orifice in a region above the orifice to cause the liquid to be broken up into droplets and to be mixed with the gas in the mixing chamber and withdrawing gas from the mixing chamber in a pulsatile flow after it has been mixed with the liquid droplets.

13. A method as in claim 12 wherein the pulses of gas delivered to the mixing chamber are also delivered to the reservoir for pressurizing the liquid in the reservoir.

14. The method as in claim 12 wherein the steps are carried out with a minimum of gas utilization.

15. A method as in claim 14 wherein the pulses of gas are delivered to the mixing chamber during an inspiratory phase and wherein the pulses of gases are withdrawn from the mixing chamber during expiratory phase.

16. A method as in claim 15 wherein the liquid is introduced into the mixing chamber during the expiratory phase.

17. A method as in claim 12 wherein the gases are delivered to the mixing chamber in a downdraft.

18. A method as in claim 12 wherein the gases are delivered to the mixing chamber in an updraft.

19. A method as in claim 12 wherein the amount of liquid delivered can be varied over a wide pressure range.

* * * * *